United States Patent [19]

White

[11] 4,436,684

[45] Mar. 13, 1984

[54] METHOD OF FORMING IMPLANTABLE PROSTHESES FOR RECONSTRUCTIVE SURGERY

[75] Inventor: David N. White, Palo Alto, Calif.

[73] Assignee: Contour Med Partners, Ltd., Mountain View, Calif.

[21] Appl. No.: 384,646

[22] Filed: Jun. 3, 1982

[51] Int. Cl.³ .............................................. B23Q 15/14
[52] U.S. Cl. .......................................... 264/138; 3/1.9; 128/92 C; 128/653; 264/163; 264/219; 378/4; 378/21; 434/82; 434/267; 434/274
[58] Field of Search ................. 434/82, 267, 270, 274; 378/4, 5, 6, 7, 8, 9, 10, 11, 12, 13, 14, 15, 16, 17, 18, 19, 20, 21; 128/303 B, 653; 264/138, 163, 219; 3/1.9; 28/92 C

[56] References Cited

U.S. PATENT DOCUMENTS

| | | | |
|---|---|---|---|
| Re. 30,947 | 5/1982 | Boyd | 250/445 |
| 2,421,609 | 6/1947 | Good | 434/267 |
| 2,852,189 | 9/1958 | Becker et al. | 318/567 |
| 3,195,411 | 7/1965 | MacDonald et al. | 409/80 |
| 3,259,022 | 7/1966 | Vietorisz | 364/561 X |
| 3,673,394 | 6/1972 | Hartmann | 364/558 X |
| 3,746,872 | 7/1973 | Ashe et al. | 378/21 X |
| 3,796,129 | 3/1974 | Cruikshank | 409/115 |
| 4,053,779 | 10/1977 | Barbieri | 378/9 |
| 4,096,390 | 6/1978 | Hounsfield | 378/5 |
| 4,145,614 | 3/1979 | Kowalski | 378/9 |
| 4,149,079 | 4/1979 | Ben-Zeev et al. | 378/9 |
| 4,298,800 | 11/1981 | Goldman . | |
| 4,352,018 | 9/1982 | Tanaka et al. | 378/4 |
| 4,360,028 | 11/1982 | Barbier et al. | 128/303 B |

FOREIGN PATENT DOCUMENTS 820576  8/1969  Canada ................................. 434/82

Primary Examiner—Donald E. Czaja
Assistant Examiner—James C. Housel
Attorney, Agent, or Firm—C. Michael Zimmerman

[57] ABSTRACT

Non-invasive method of forming prostheses of skeletal structures internal to a body for use in reconstructive surgery. The selected internal skeletal structure is measured by subjecting the body to radiant energy to produce radiant energy responses that are detected to obtain representations delineating the skeletal structure. Three dimensional coordinate data defining the skeletal structure is generated from the obtained representations. The coordinate data is employed to control a sculpting tool to form the prosthesis.

31 Claims, 14 Drawing Figures

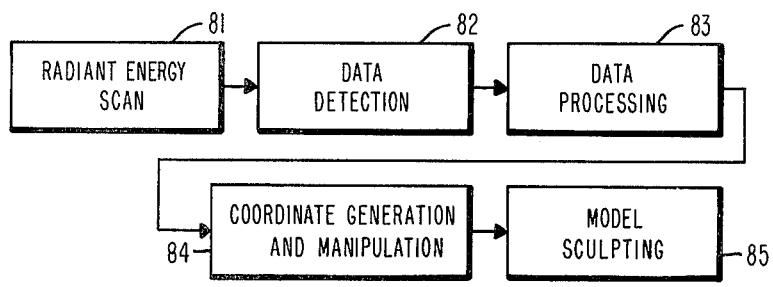
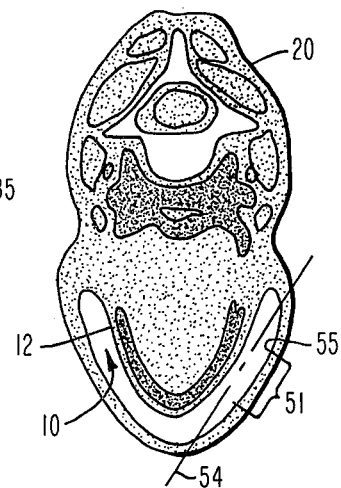
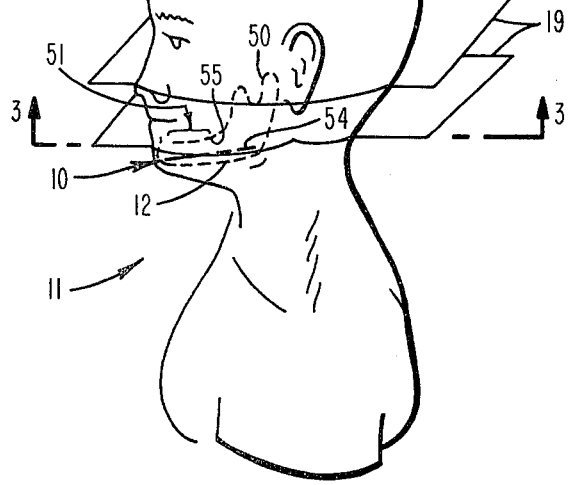
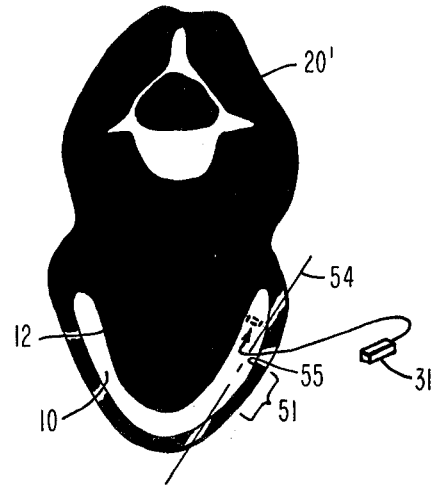
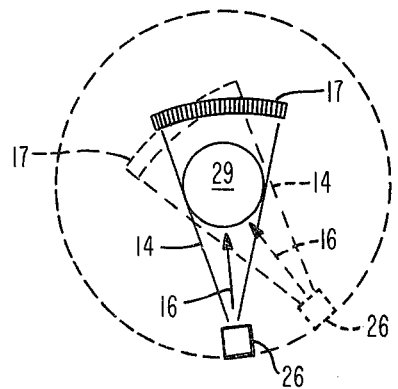
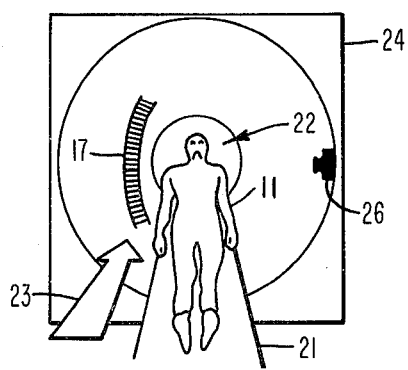

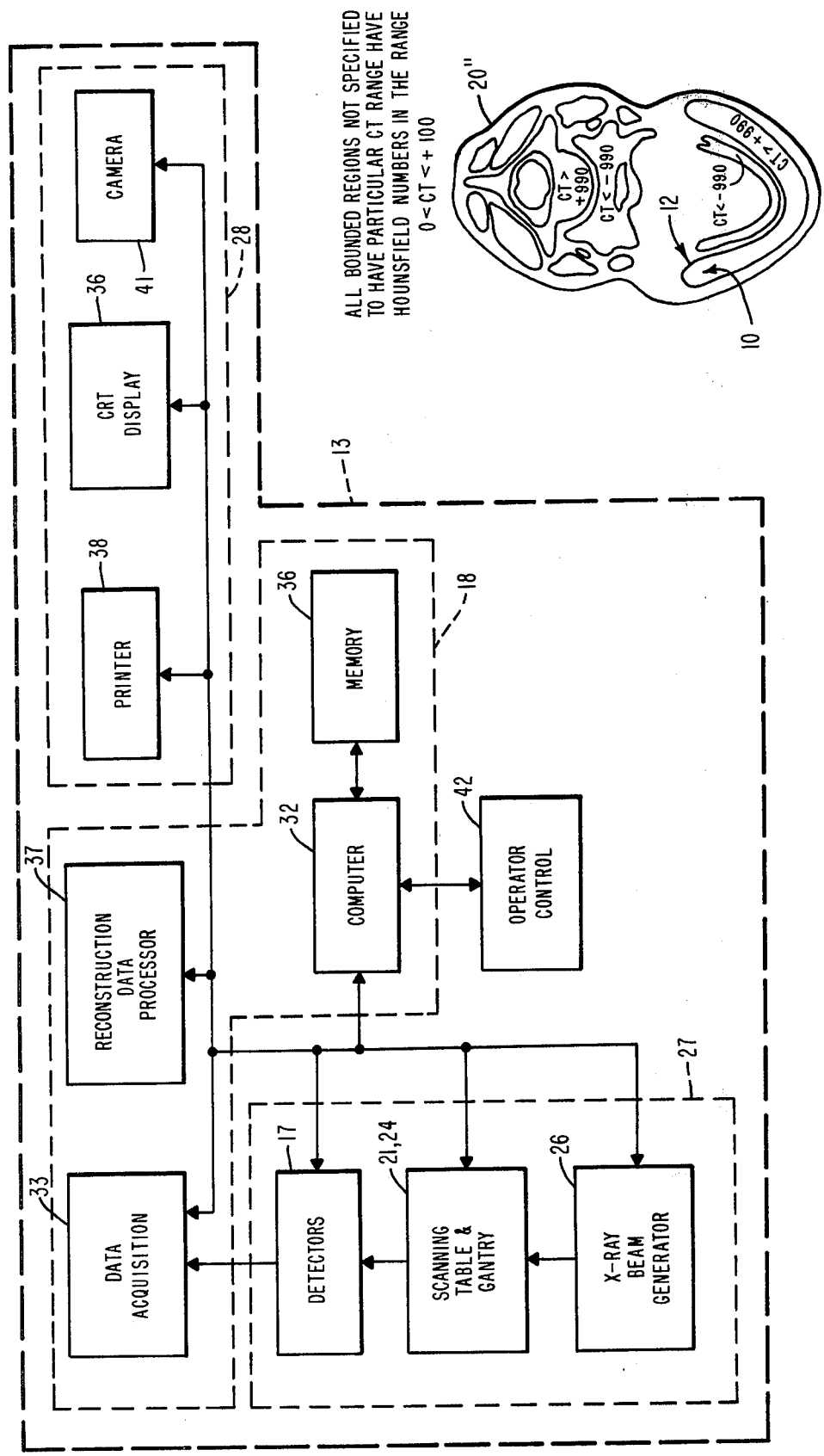

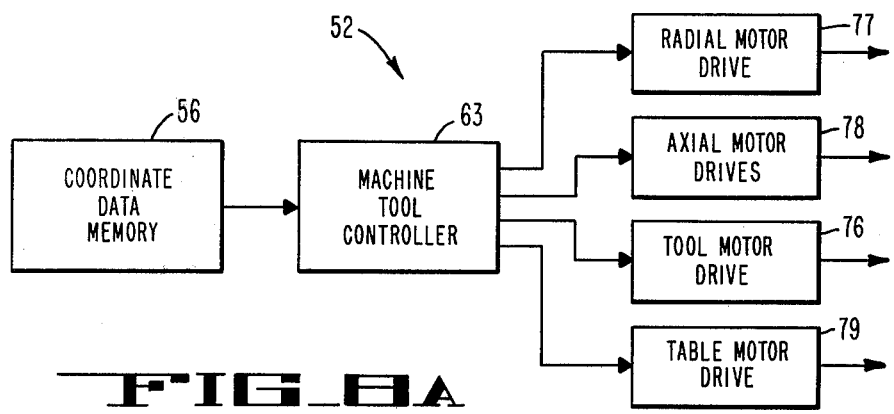
FIG_8A
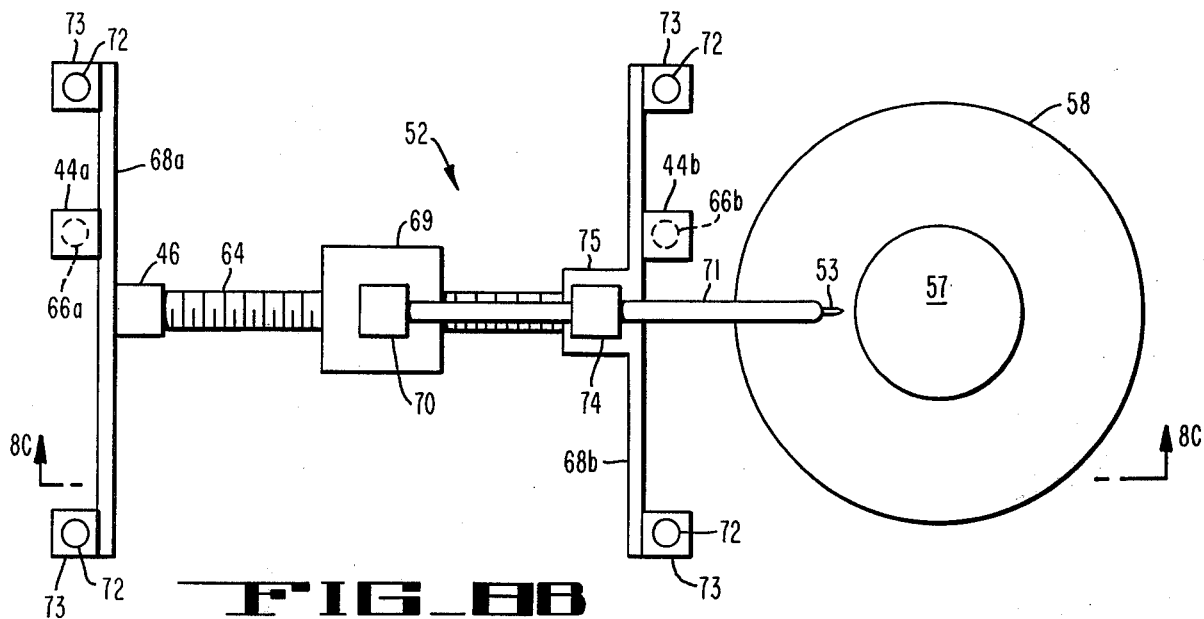
FIG_8B
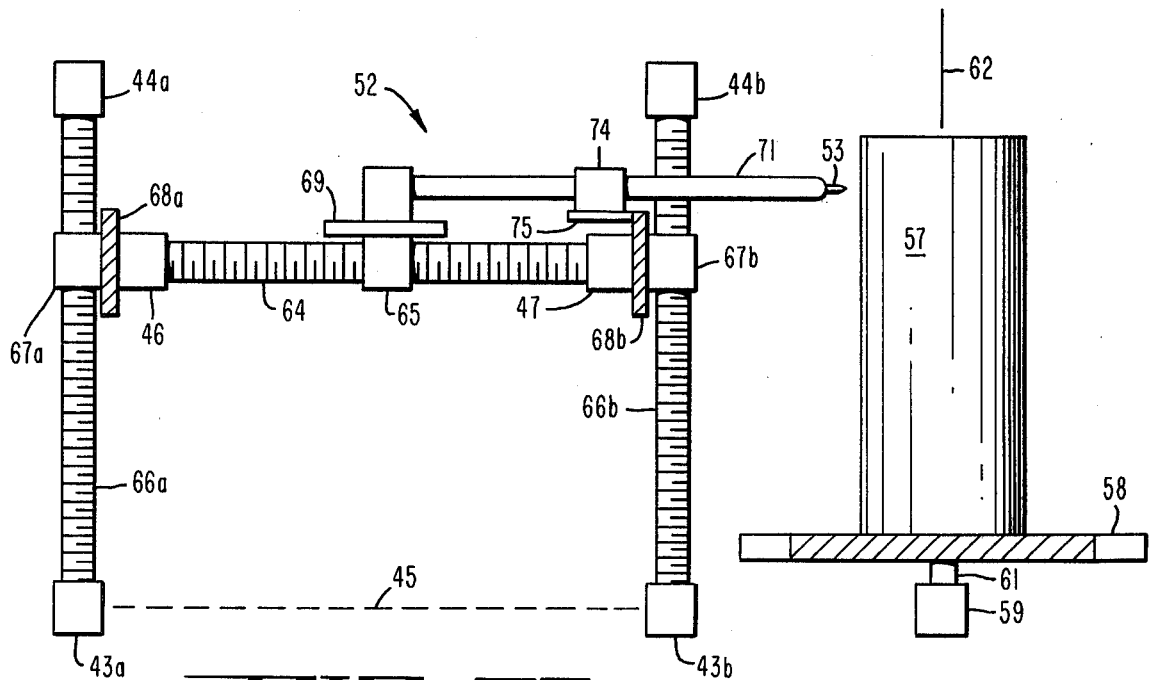
FIG_8C

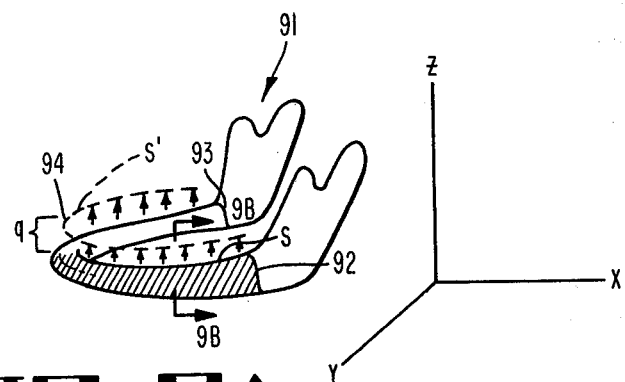
FIG_9A
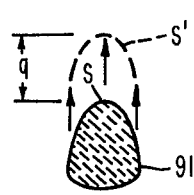
FIG_9B
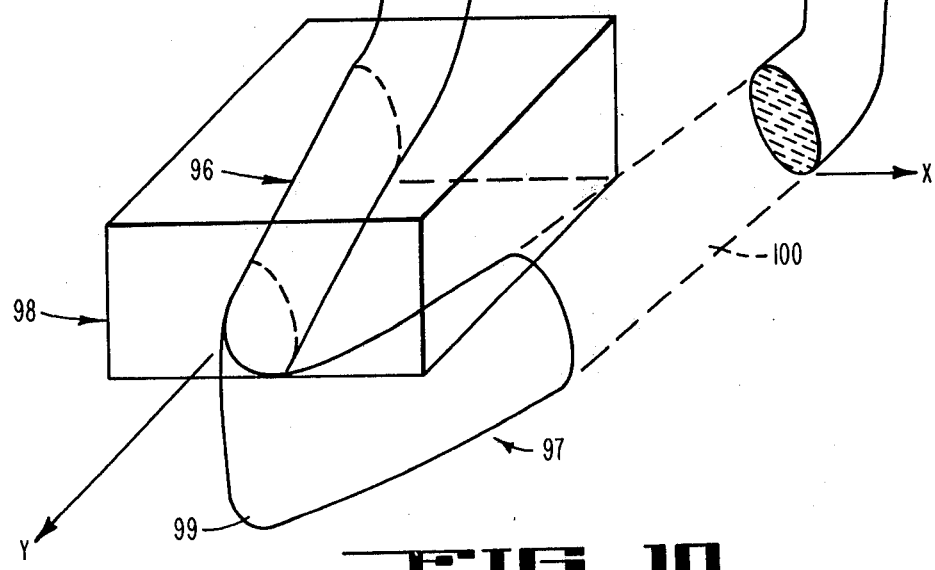
FIG_10

METHOD OF FORMING IMPLANTABLE PROSTHESES FOR RECONSTRUCTIVE SURGERY

DESCRIPTION

The present invention relates generally to a method of constructing three dimensional corporeal models of structures internal to bodies and, more particularly, to a method of constructing such models from three dimensional representations of the internal structures obtained without physical invasion of the bodies.

A three dimensional corporeal model of a structure whose exact size and/or shape is unknown ordinarily is constructed from direct measurement of the dimensions of the structure. Direct measurement of the internal structure has the advantage of providing precise dimensional information that enables the construction of a corporeal model which accurately represents the internal structure. Often, however, the structure is confined within a body so as not to be accessible for direct measurement. In such cases, the body is either opened or disassembled to provide access for the measurement of the internal structure of interest. When such opening or disassembly has not been practicable or desirable, corporeal models have been constructed with the aid of visual inspections of standard radiographic images of the internal structure of interest, externally formed castings of the body and other techniques of indirect examination of the body. The deficiencies of such techniques, however, have made it difficult to construct corporeal models that accurately represent internal structures. For the most part, such indirect examination techniques are deficient for such purposes because they provide imprecise dimensional information and structural delineation of structures internal to a body.

Accuracy is particularly important in the construction of corporeal models of internal tissue structures of mammalian anatomies. Such models will be referred to herein as prostheses, whether in the form of a surgically implantable prosthesis or an external prosthesis. Though exact measurement and accurate conformation are desirable in the construction of implantable prostheses for reconstructive surgery, non-invasive direct measurement of internal anatomic tissue structures is not available by present methods and not practicable for the fabrication of prostheses. Present methods require fabrication of an implantable prosthesis for correction of bony contour abnormalities on the basis of a plaster casting taken over the area of abnormality with soft tissue interposed between the structural defect and the cast. From this case, a model onlay prosthesis is constructed by a hand-sculpting method by a skilled prosthetist on a best-approximation basis, attempting to allow for the inaccuracies resulting from indirect measurement. Residual inaccuracies must then be modified at the time of implantation when direct surgical examination of deep structures is possible.

If a bone graft from the patient is to be fashioned to correct a structural defect, the surgeon has no precise representation of the bony abnormality prior to direct examination at the time of surgery, and is then required to alter the abnormality and fashion the implant in the operating room without the benefit of a prior working model.

Construction of accurate preoperative models and correctional implants avoids the shortcomings of the above-noted hand sculpting technique and diminishes the morbidity associated with the prolonged anesthesia presently required.

The present invention is a method of constructing a three dimensional corporeal model that accurately represents a selected structure internal to a body. The internal structure is measured by subjecting the body to radiant energy to produce radiant energy responses that are detected to obtain representions delineating the internal structure three dimensionally. A set of three dimensional coordinates defining a three dimensional representation of the selected internal structure is generated from the obtained representations and is employed to direct a sculpting tool to form a corporeal model of the selected structure. As will become more apparent upon consideration of the detailed description of a preferred embodiment of the method of the present invention found hereinafter, the formation of an accurate corporeal model replica of the selected structure is facilitated by using the generated set of three dimensional coordinates to control the trajectory of a machine-controlled sculpting tool for the purpose of formng the corporeal model. However, the method of the present invention can be practiced to provide three dimensional coordinates that define a mold cavity model representation of the selected structure from which one or more corporeal model replicas may be formed by conventional molding processes. In such implementations, the trajectory of the sculpting tool is directed by the provided three dimensional coordinate data to form the desired mold cavity.

As will become more apparent upon consideration of the description of the preferred embodiment of the present invention, noninvasive radiographic image reconstruction techniques and automatically controlled machining techniques are adapted and combined to enable the precise measurement of internal structures and the construction of corporeal models that are accurate representations of the internal structures. A radiographic image reconstruction technique particularly useful in the method of the present invention is computed tomography, according to which a cross sectional tomographic image is constructed from radiant energy transmitted through or reflected from the interior of the body along paths at different angles relative to the body. The image is constructed by computer manipulation of the detected radiant energy according to an algorithm whereby the localized radiant energy responses occurring at the cross section location of the body are computed. The computed radiant energy responses are characteristic of the substances located at the cross section location of the detected radiant energy responses and, therefore, enable formation of an image of the structure at the cross section location. A series of such images is obtained at locations distributed along a line perpendicular to the plane of cross section by subjecting the body to radiant energy and detecting the transmitted or reflected radiant energy at each of the distributed locations. Computerized tomographic devices have employed x-ray, nuclear magnetic resonance (NMR), positron emission (PET) and ultrasonic radiant energy techniques to obtain data for the construction of images of internal structures. Both analog gray-scale pictures of the detected radiant energy responses and paper printouts of mapped numerical value representations of the gray-scale values are commonly provided by such computerized tomographic devices. Examples of such devices are described in U.S. Pat. Nos.

3,673,394, 4,298,800 and Re 30,397, and references cited in the patents.

Machine-controlled contour sculpting tool devices have been widely used to reproduce three dimensional object surfaces from representations of such surfaces. Some of these devices control tool trajectory relative to a work piece in accordance with numerical data obtained from drawings or photographs of the desired object, for example, by the use of contour or profile following instruments. Other contour sculpting devices utilize contour followers adapted to follow a physical model of the desired object and generate coordinate control data used to control the trajectory of the sculpting tool. Some contour followers are mechanically linked to the sculpting tool whereby movement of the contour follower directly causes corresponding movement of the sculpting tool. Examples of contour sculpting tool devices are described in U.S. Pat. Nos. 2,852,189, 3,195,411, 3,259,022 and 3,796,129.

In the preferred embodiment of the method of the present invention, a computerized x-ray tomographic device is operated to provide representations of the absorption coefficient of substances at locations internal to a body. The absorption coefficient representations delineate the internal structures and are examined to derive three dimensional coordinate data defining a three dimensional representation of a selected delineated internal structure. The coordinate data is derived in a format compatible with a machine-controlled sculpting tool device selected to form the desired corporeal model of the selected internal structure. A model is formed from a workpiece of suitable material by operating the machine-controlled sculpting tool device to control the trajectory of its cutting sculpting tool relative to the workpiece in accordance with the coordinate data derived from the absorption coefficient representations of the structure obtained by the computerized x-ray tomographic device.

The foregoing and other objects, advantages and features characterizing the present invention will become more apparent upon consideration of the following description of specific embodiments and appended claims taken together with the drawings of which:

FIG. 1 is a diagram schematically illustrating the steps of the preferred embodiment of the method of the present invention for obtaining three dimensional coordinate data of a selected structure internal to a body and generating a corporeal model thereof;

FIG. 2 is a perspective view of a head illustrating the manner in which three dimensional coordinates defining a selected internal anatomic structure are obtained in accordance with the preferred embodiment of the method of the present invention;

FIG. 3 is a schematic diagram of an exemplary grayscale tomographic axial image in a plane taken at lines 3—3 of FIG. 2, with the image constructed from x-ray radiation responses obtained from the plane in accordance with the preferred method of the present invention;

FIG. 4 is a schematic diagram of an enhancement of the exemplary image of FIG. 3 depicting a cross section of a mandible selected to be constructed in model form in accordance with the preferred method of the present invention;

FIGS. 5A and 5B are schematic diagrams illustrating x-ray scanning equipment for obtaining radiation responses from cross sections of a body in accordance with the preferred method of the present invention;

FIG. 6 is a schematic block diagram of a computerized x-ray tomographic apparatus for practicing the preferred method of the present invention;

FIG. 7 is a schematic representation of an exemplary print of a mapped numerical value representation of a reconstructed tomographic image;

FIGS. 8A, 8B and 8C together comprise a schematic diagram of a machine-controlled sculpting tool apparatus for forming corporeal models of selected structures in accordance with the preferred method of the present invention;

FIGS. 9A and 9B together comprise a schematic diagram illustrating the construction of an onlay prosthesis from three dimensional coordinate data translated in accordance with the preferred method of the present invention; and FIG. 10 is a schematic diagram illustrating the construction of an inlay prosthesis from three dimensional coordinate data translated in accordance with the preferred method of the present invention.

The method of the present invention will be described with reference to a preferred embodiment of the present invention arranged to construct a prosthesis of an internal anatomic tissue structure from three dimensional coordinate data defining the internal structure obtained without the physical invasion of the anatomy. As will be appreciated from the following description of the preferred embodiment, however, the method of the present invention can be practiced to obtain definitive three dimensional coordinate data and construct corporeal models of structures internal to bodies other than anatomies.

Generally and referring to FIG. 1, a corporeal model representation of a selected internal structure of a body is constructed by controlling a sculpting tool to follow a trajectory relative to a workpiece determined by three dimensional coordinate data that specifies the contour of the selected internal structure. To obtain the three dimensional coordinate data in accordance with the method of the present invention, the selected internal structure is scanned as step 81 by subjecting it to radiant energy to produce radiant energy responses that delineate the selected structure three dimensionally and are detectable at a location exterior to the body. The radiant energy responses are detected at step 82 and the detected responses processed at step 83 to obtain data delineating the selected structure three dimensionally. At step 84, the three dimensional coordinate data required for the control of the sculpting tool in constructing the desired corporeal model representation of the selected internal structure is generated from the data provided by the performance of step 83. As briefly discussed hereinbefore and as will become more apparant upon consideration of the detailed description of the preferred embodiment of the method of the present invention to follow, various corporeal model representations of a selected structure can be constructed in accordance with the present invention. A scale replica of the internal structure in the state found within the body is constructed from three dimensional coordinate data defining the selected structure at scale. If other than a scale replica of the internal structure is desired, data is manipulated at step 84 to obtain transformed three dimensional coordinate data for constructing an altered corporeal model representation of the selected internal structure. The manipulation can be performed at the time of the generation of three dimensional coordinate data from the data provided by the performance of step 83, for example, by generating the three dimensional coordinate data according to an algorithm relating the untransformed three dimensional coordinate data to the desired transformed three dimensional coordinate data. Alternatively, the transformed three dimensional coordinate data can be obtained by manipulation of generated untransformed three dimensional coordinate data, by manipulation of the data delineating the selecting structure before the generation of the three dimensional coordinate data or by combinations of the aforementioned manipulations. As will be described in further detail hereinafter with reference to the preferred method of the present invention, interpolating, form or curve fitting, scaling and translating are manipulations particularly useful in constructing external and implantable prostheses and mold cavities for casting models of selected internal structures. In any case, the three dimensional coordinate data is generated in a format determined by the sculpting device used in constructing the corporeal model representation of the selected internal structure. The desired corporeal model representation is obtained at step 85 by directing a sculpting tool in accordance with the generated three dimensional coordinate data to follow a trajectory relative to a workpiece that produces the representation defined by the three dimensional coordinate data. The corporeal model is fabricated from suitable material selected according to the expected use of the model. Examples of material suitable for the construction of prostheses are Silastic and Proplast. "Silastic" is a trademark of Dow Corning Corporation used to identify the material it markets. "Proplast" is a trademark of Vitek, Inc. used to identify the material it markets.

A preferred embodiment of the method of the present invention arranged to construct corporeal models of internal anatomic tissue structures will now be described in detail with reference to FIGS. 2-7. The preferred embodiment will be described in connection with the construction of prostheses of a mandible. More specifically and referring to FIGS. 2-4, the mandible 10 of the anatomy 11 is specified three dimensionally by subjecting the anatomy to radiant energy to produce radiant energy responses within the anatomy that are characteristic of a selected physical property of substances of and detectable at the exterior of the anatomy. Different substances of the anatomy 11 produce different distinguishable characteristic radiant energy responses which, upon detection, provide distinguishable representations of the different substances located within the anatomy. As will be described in greater detail hereinafter, a computerized tomographic imaging device 13 (FIG. 6) utilizing x-ray radiation is employed in the practice of the preferred embodiment of the method of the present invention to obtain distinguishable representations of different substances within the anatomy 11. As described hereinbefore, computerized tomography devices provide cross sectional representations of the internal structure of the anatomy 11 reconstructed from radiant energy transmitted through or reflected from the interior of the anatomy along paths at different angles relative to the anatomy. In the x-ray tomographic device 13, a narrow x-ray beam 14 (FIGS. 5A and 5B) is directed through the anatomy 11 along several paths (such as depicted by arrows 16) in a plane and the radiation transmitted through the anatomy is measured by x-ray detectors 17. A transmission measurement taken along each path represents a composite of the absorption characteristics of all elements in the path of the beam. A computerized data processing system 18 (FIG. 6) associated with the x-ray tomographic device 13 manipulates the measurements taken along the several paths according to an algorithm to calculate the attenuation coefficient of elements in each XY plane 19 (FIG. 2) through which the x-ray beam 14 is directed. The attenuation coefficients of elements in other planes distributed at spaced locations along the Z axis perpendicular to the XY planes 19, hence the x-ray beam 14, are obtained by relatively moving the body 11 and the x-ray generation and detection apparatus in increments along a line generally perpendicular to the plane of the x-ray beam. Typically, the body 11 is moved through a stationary scanning station at which the x-ray measurements along the several paths in each XY plane are obtained by rotating oppositely disposed x-ray generator 26 and x-ray detector 17 devices (FIGS. 5A and 5B) about the body. The calculated attenuation coefficients provide accurate representations of the densities of the substances within the anatomy. In the processing of the measurements, gray-scale values are assigned to the calculated attenuation coefficient values to provide representations of the elements in each plane 19 suited for displaying an image of the structure of the anatomy 11 at the location of the plane.

For example, FIGS. 3 and 4 schematically illustrate different image reconstructions 20 and 20' respectively, of a single cross section of the anatomy 11 shown in FIG. 2 taken at a plane 19 extending through the mandible 10. As can be seen by inspection of FIGS. 3 and 4, the light gray scale mandible representative values 10 are readily distinguishable from the darker surrounding gray scale representations of other substances. Greater contrast between the mandible representative gray scale values and the gray scale representations of other anatomic tissue substances at the cross section can be obtained by enhancing the image reconstruction in the manner described hereinafter and shown in FIG. 4. In both image reconstructions of FIGS. 3 and 4, the gray scale representations clearly delineate the surface location 12 of the mandible 10, from which the three dimensional coordinates of the mandible are derived. A series of such gray scale cross sectional representations of the anatomy 11 obtained along the Z axis provides information from which three dimensional coordinate data can be derived. As will be described in further detail hereinafter, three dimensional coordinate data specifying a selected structure 10 of which a model is to be constructed is derived from a series of such cross sectional representations of the anatomy 11.

As mentioned hereinbefore, other noninvasive radiographic imaging devices can be utilized in the practice of the method of the present invention to obtain cross sectional representations of the body 11 from which the desired three dimensional coordinate data defining the structure 10 of interest can be obtained. In PET devices, for example, radiant energy originates within the anatomy 11 from an intravenously administered biologically active substance labeled with a positron-emitting radioactive isotope. The isotope decays by emitting positrons that travel a short distance in tissue before colliding with electrons. A collision between a positron and electron annihilates both particles, converting the mass of the two particles into energy divided equally between two gamma rays emitted simultaneously along oppositely directed paths. One PET device in use includes arrays of scintillation detectors encircling the subject supported by a mobile table with the region of interest at the axis about which the detectors are disposed. The arrays of detectors record simultaneously emitted gamma rays at a plurality of spaced axial cross sections of the subject during an imaging cycle, the detectors being linked in opposite pairs so that emitted gamma rays are recorded only when both detectors of a pair simultaneously sense gamma rays. All gamma ray pairs originating within a volume of the subject defined by the cylindrical, colinear field of view joining paired detectors are sensed. Gamma rays orginating outside that volume are not sensed by the detectors. The sensed gamma ray responses are processed to obtain representations delineating the substances in the field of view. The mobile table moves the subject axially relative to the encircling detectors to enable the detection of radiant energy events and concomitant generation of representations of substances at a plurality of spaced axial cross sections of the subject.

NMR imaging devices have the advantage of using a non-ionizing form of radiant energy. In NMR devices, the subject is placed in a strong magnetic field while a brief high frequency signal is beamed at the body. Different atoms of substances of the body respond by sending out different characteristic radio signals that are detected by tunable receiving antennas placed about the body. The tunable receiving antennas are adjusted to be responsive to selected radio signals and thereby obtain representations of selected substances, which are processed by an associated computerized data processing system to generate a distinguishable characteristic representation of such substance in a plane of the subject. Representations of substances in other parallel planes at spaced locations along a defined line are obtained by moving the subject in increments through the magnetic field and past the receiving antennas.

Ultrasonic radiographic imaging devices also can be employed to obtain representations of the internal structure of a body. Like NMR imaging devices, ultrasonic devices have the advantage of using a non-ionizing form of radiant energy in obtaining the data from which representations of the internal structure of bodies are derived. Most ultrasonic imaging devices generate representations of anatomic structures from detected reflections of high frequency pulsed sound waves directed through the anatomy. A series of pulsed sound waves are sent forth into the anatomy by electrically pulsed piezoelectric transducers in contact with the anatomy. The transducers employed are capable of reversibly converting electrical to vibratory mechanical energy at the pulse frequency of interest. After the transmission of each short burst or pulse of sound energy, the circuitry associated with the transducer is switched to act as a receiver for returning or reflected echos of the transmitted sound waves. Echos are reflected when the pulsed sound encounters an interface of tissues of different densities. Tissues of different acoustic impedances return different echos. The reflected echos are converted to representative electrical signals by the piezoelectric transducers, from which planar representations of the internal structure of the anatomy are obtained. The data processing system associated with the ultrasonic device converts elapsed time between transmission of a sound pulse and reception of each echo into a measurement of the distance from the transducer to each location of echo reflection.

Each of the radiographic imaging devices described above provides representations of the internal structure of a body by subjecting the body to selected radiant energy. In x-ray, NMR and ultrasonic devices, the body is subjected to radiant energy projected at it from a location external to the body. With PET devices, however, the body is subjected to radiant energy generated within the body itself. In any case, each of the imaging devices produces radiant energy responses within a body from which distinguishable representations of different internal structures of the body are generated and from which, in turn, three dimensional coordinates defining a selected structure internal to the body are generated for directing a sculpting tool to form a corporeal model representation of the selected internal structure.

A computerized x-ray tomographic system suited for use in obtaining three dimensional coordinate data defining the mandible 10 of the anatomy 11 in accordance with the preferred embodiment of the method of the present invention is marketed by General Electric Company under the model designation CT/T 8800 Scanner System. The preferred method of obtaining three dimensional coordinate data defining the mandible 10 in accordance with the present invention will now be described with reference to the CT/T 8800 Scanner System, which is schematically illustrated in FIGS. 5 and 6. The computerized x-ray tomographic system 13 (FIG. 6) is arranged to produce computer reconstructed cross sectional images of any part of the anatomy from multiple x-ray absorption measurements. The system 13 includes a radiation scanning assembly 27 having a mobile table 21 (FIG. 5B) for supporting and transporting a subject through the x-ray scanning station 22 along a path indicated by arrow 23. The table 21 is configured to aid in centering and confining the anatomy 11 in a selected orientation relative to the x-ray generator 26 and detector 17 (FIGS. 5A and 5B) of the scanning assembly.

The radiation scanning assembly 27 also includes a gantry 24 (FIG. 5B) positioned along the path 23 for supporting the x-ray generator 26 and x-ray detector 17 for rotation about the mobile table 21 in a selected plane perpendicular or at an angle to the path 23. The x-ray generator 26 emits an x-ray fan beam 14 that is directed at an array of x-ray radiation sensitive cells forming the detector 17 at the opposite side of the gantry 24. The beam 14 is formed and the detector 17 is arranged to permit scanning of an object detection zone 29 (FIG. 5A) located in the plane of the beam. Each cell of the detector 17 detects a portion of the x-ray beam 14 after its passage through the object detection zone 29 (and any part of a body 11 located in the zone) and provides data representative of the composite x-ray radiation attenuation coefficient along a path between the x-ray generator 26 and the data cell. The data provided by the detector 17 as it and the X-ray generator 26 are rotated about the subject (borne by the table 21) is processed to generate an attenuation coefficient representation for each volume element 31 (FIG. 4) of the cross sections of the anatomy 11 scanned by the x-ray beam 14. The resolution capability of the CT/T 8800 system 13 is dependent upon the fan thickness of the x-ray beam 14 and the power of the data reconstruction algorithm characterizing the software program employed in the system. A typical CT/T 8800 system generates an attenuation coefficient representation for a volume element 31 having a size on the order of 1.5 mm×0.8 mm×0.8 mm, with the long 1.5 mm dimension of the volume element 31 extending in the direction of the fan thickness dimension of the beam 14, hence the cross section of the anatomy 11 scanned. The other dimensions of the volume element 31 in the plane of the scanned cross section are largely determined by the software program, and attenuation coefficient representations of volume elements of smaller dimensions in the plane of the scanned cross section can be obtained by increasing the power of the data reconstruction software program.

Once the anatomy 11 is positioned as desired relative to the scanning station 22, the mobile table 21 and gantry 24 are operated in sequence under control of the computer 32 to (i) position the anatomy 11 within the scanning station 22 at the desired location along path 23, (ii) rotate the x-ray generator 26 and detector 17 for subjecting a cross sectional slice of the anatomy to the x-ray beam 14 and detecting the resulting radiation responses, and (iii) increment the table 21 a distance of 1.5 mm for scanning another cross sectional slice of the anatomy with the x-ray beam. This operation of the table 21 and gantry 24 continues until data from the desired number of cross sectional slices of the anatomy 11 is obtained. Data from each cross sectional slice is obtained by pulsing the x-ray generator 26 to send pulses of x-ray radiation through the cross sectional slice along several hundred different paths while the gantry 24 is operated to rotate the x-ray generator 26 and detector 17 about the anatomy 11. This provides the radiation responsive data from which cross sectional representations of the anatomy are reconstructed.

The radiation responses detected by the detector 17 are processed by data acquisition circuitry 33 (FIG. 6) of the system 13 under control of the computer 32 for storage in a memory 36. A reconstruction data processor 37 is controlled by the computer 32 to reconstruct cross sectional representations of the anatomy 11 from the stored data. More specifically, the reconstruction data processor circuitry 37 is controlled by the computer 32 to manipulate the stored data mathematically according to a reconstruction algorithm to calculate the attenuation coefficient for each volume element 31 (FIG. 4) of each cross sectional slice of the anatomy 11. The calculated attenuation coefficient data is stored in the memory 36 for use as needed. For image display purposes, the calculated attenuation coefficients are converted to gray scale values expressed numerically in Hounsfield units, commonly referred to as "CT numbers".

The computerized data processing system 18 is operable through an operator control system 42 to construct various selectable representations of the anatomy 11 from the detected radiation response data. For example, the cross sectional representations of the anatomy can be enhanced by selectively narrowing the gray scale range and/or offsetting the gray scale range relative to the range of attenuation coefficients of substances found in the anatomy. FIGS. 3 and 4 schematically illustrate an example of the enhancement of the cross sectional representations of the anatomy 11. In the illustrated example, volume elements 31 having attenuation coefficients within a selected range or window are assigned one gray scale value, such as white, while all volume elements having attenuation coefficients outside the selected range or window are assigned a black gray scale value. In this example, the gray scale range is centered at the end of the range of attenuation coefficients where that of bone is found. The operator control system 42 also enables the detected radiation response data to be manipulated to reconstruct sagittal and coronal cross section representations of the anatomy 11 at one or more selected planes orthogonal to the axial plane of the anatomy. Each of the aforementioned reconstructed cross section representations accurately protrays the internal structure of the anatomy 11 at the cross section location of the representation and, therefore, may be used in deriving three dimensional coordinate data for use in constructing corporeal models of internal structures of the anatomy.

Data from which the desired three dimensional coordinate information can be derived is available from the computerized x-ray tomographic system 13 in various formats. Digital data representations of the reconstructed cross sections of the anatomy 11 are stored in the memory 36 and are accessible for use in generating the three dimensional coordinate data. In addition, the system 13 includes an image generation system 28 which is operable to provide a paper printout image in the form of mapped numerical value representations of the reconstructed cross section of the anatomy 11, an analog display of gray scale pictures of the reconstructed cross section, or hard copies of the analog gray scale pictures. More specifically, printouts of mapped numerical value representations of selected reconstructed cross sections of the anatomy 11 is provided by a printer 38 included in the image generation system 28. Analog gray scale pictures of the reconstructed cross sections can be viewed on the CRT display 39 and hard copies obtained from the x-ray film camera 41.

Control of the computerized x-ray tomographic system 13 in generating reconstructed representations of cross sections of the anatomy 11 is exercised by the operator through the operator control system 42. Inasmuch as General Electric Company's CT/T 8800 Scanner System and operator manuals therefor are available from which further details of the construction and operation of system 13 can be determined, such details are not described herein.

To obtain three dimensional coordinate data of the mandible 10 illustrated in FIG. 2, the system 13 is operated to obtain radiation response data from a plurality of contiguous 1.5 mm axial cross sections of the entire mandible. The radiation response data is processed to reconstruct representations of each axial cross section 20, such as illustrated in FIG. 3. To facilitate the reconstruction and use of the axial cross section data, each axial cross section representation is enhanced as illustrated in FIG. 4 to distinguish bone substance from all other substances located at the position of each axial cross section 20'.

Three dimensional coordinate data defining the mandible 10 can be obtained directly from the digital data generated by the computerized x-ray tomographic system 13 and stored in its memory 36. For example, the system 13 generates and manipulates reconstructed digital data representations of cross section volume elements according to the spatial coordinates of the represented volume elements. By accessing such representations within the system 13 according to their spatial coordinates, the three dimensional coordinates of the surface 12 of the mandible 10 can be obtained directly and automatically from the data stored in the memory 36 of the system.

Three dimensional coordinate data also can be obtained directly from analog gray-scale pictures of the reconstructed representations of the axial cross sections, such as illustrated in FIG. 4. Each of the series of pictures of the axial cross sections 20' is composed of known gray scale values from which two planar coordinates is determined, such as X and Y. The distribution of gray scale values in the axial direction, as represented by the series of pictures of axially disposed contiguous cross sections of the anatomy at locations including the mandible 10, provides data from which the third coordinate, Z, is determined. The spatial coordinates defining the three dimensional surface of the mandible 10 is determined from the coordinate location of the gray scale value representation of the surface 12. This coordinate determination can be accomplished through various measuring methods, including manually defining analog prints or displays of each cross section 20' in terms of spatial coordinates. Alternatively, the determination of the coordinates can be carried out through the use of mechanical aids, such as contour or profile follows. Such aids are used to determine the XY planar coordinates of the reconstructed surface representation 12 in each cross section 20', the third coordinate being given by the axial coordinate Z of each reconstructed cross section. If all reconstructed cross section representations of the mandible 10 are employed in the generation of the three dimensional coordinate data, the Z axial coordinate data is distributed at intervals corresponding to the center-to-center spacing of the cross sections of the body 11 represented by the reconstructed data. When the reconstructed data is obtained from contiguous cross sections of the body, the Z axial coordinate data is at intervals of 1.5 mm.

Printouts of mapped numerical value representations of the reconstructed absorption coefficients of the volume elements of each reconstructed cross section also can be used to obtain three dimensional coordinate data defining the surface 12 of the mandible 10. FIG. 7 is a schematic illustration of such a printout. To facilitate the illustration of a mapped numerical value image of a reconstructed cross section of the anatomy 11, a reconstructed cross section 20" of the anatomy is divided by lines into regions of identified significant numerical values. The lines also are used to identify surface boundaries of significant structures internal to the anatomy 11. As discussed hereinbefore, the reconstructed attenuation coefficients are expressed as a Hounsfield unit and are commonly referred to as "CT numbers". In the CT/T 8800 system 13, the range of CT numbers extends from −1000 (which represents air) to +1000 (which represents dense bone). A CT value of 0 represents water. The three dimensional coordinate data defining the surface 12 of the mandible 10 can be obtained from the printouts of mapped CT values in the ways described hereinbefore with reference to the use of analog gray scale pictures or displays of reconstructed axial cross sections. When using printouts of mapped CT values defining reconstructed cross sections 20" of the mandible, the three dimensional coordinates defining the surface of the mandible are determined by following the contour of numerical CT values delineating the reconstructed surface 12 of the reconstructed mandible 10, instead of the contour delineated by a line in an analog gray scale picture or display.

A preferred method of sculpting a corporeal model of a segment 51 (FIGS. 2-4) of the mandible 10 in accordance with the present invention will now be described with reference to the machine-controlled contour sculpting tool apparatus 52 illustrated in FIGS. 8A-8C. The machine-controlled sculpting tool apparatus 52 is arranged to control a cutting tool 53 in accordance with cylindrical coordinates defining the shape of the desired corporeal model representation of the mandible 10.

Therefore, the reconstructed tomographic representations of the anatomy 11 generated by the computerized x-ray tomographic system 13 illustrated in FIG. 6 are utilized to derive radial (r), angular ($\theta$) and axial (z) coordinates describing the surface 12 of the mandible segment 51 relative to a selected reference line. Preferably, the selected reference line in a straight line passing through a point lying along the centric of the mandible segment 51. The reference line is depicted in FIGS. 2, 3 and 4 by a broken line 54 of alternate long and short lengths. The axial coordinate z extends along the reference line 54, and the radial r and angular $\theta$ coordinates are in plane perpendicular to the reference line 54. The deriviation of the cylindrical coordinates relative to the reference line 54 is facilitated by positioning the subject within the scanning station 22 and/or tilting the gantry 24 relative to the mobil table 21 so that the reference line 54 is generally perpendicular to the plane of the x-ray beam 14. In this way, the x-ray tomographic system 13 is operated to provide a series of oblique (i.e., other than axial, coronal or saggital) cross sectional representations of the mandible segment 51 in parallel planes distributed along and perpendicular to the line 54, with of each cross sectional representation centered on the line 54. Such positioning reduces the amount of data processing time required to obtain the cross sectioned representations from the detected radiant energy response and, hence, the three dimensioned coordinates of interest. However, such subject positioning and/or gantry tilting is unnecessary when a radiographic tomographic system 13 is employed that is capable of reconstructing oblique cross section representations of internal anatomic structures from radiant energy responses obtained from a subject oriented in the standard supine position with the axis of the body perpendicular to the cross sections of the body from which the radiant energy responses are obtained.

A workpiece of a material suitable for constructing the desired prosthesis is secured to a rotatable turntable 58 that is coupled to a drive motor 59 by a drive shaft 61. To form the desired model, the drive motor 59 rotates the workpiece 57 about the axis 62 as the trajectory of the cutting tool 53 is controlled to form the desired contour in the workpiece. The axis 62 of rotation of the workpiece 57 is located to pass through the origin relative to which the cutting tool 53 is moved in the radial and axial directions in accordance with the cylindrical coordinates. The origin is located at a point along reference line 54 (FIGS. 2-4), which for convenience is selected to be at one end 55 of the mandible segment 51 being modeled. In the example, the origin is located at the end 55 of the mandible segment 51 closest to the hinge segment 50 of the mandible 10. In generating the three dimensional cylindrical coordinates from the data obtained by the x-ray tomographic system 13, the cylindrical coordinates are specified relative to an origin that is to be coincident with the origin of the coordinate system used in the sculpting tool apparatus 52 to specify the spatial location of the cutting tool 53. The origin of the coordinate system of the sculpting tool apparatus illustrated in FIGS. 8A-8C is located a short distance above the turntable 58.

The cutting tool 53 is moved in the axial z and radial r directions relative to the axis 62 in accordance with the cylindrical coordinate data by cooperating way and carriage assemblies. Movements in the radial direction, r, are governed by a horizontally extending way 64 and a cooperating carriage 65 that carries the cutting tool 53 for movement along the horizontal way. Movements in the axial direction, z, are governed by a pair of vertically extending ways 66a and 66b and cooperating carriages 67a and 67b that support the horizontal way 64 for movement along the vertical way. In the preferred embodiment, the ways 64 and 66 are motor driven lead screws that engage lead screw nut assemblies forming the cooperating carriages 65 and 67. More specifically, each of the vertical lead screws 66a and 66b extends between one of the reversible motors 43a and 43b and one of the cooperating journals 44a and 44b. The driven end of each lead screw is coupled for rotation by the operatively associated motor and the opposite end of that lead screw is seated for rotational support within the cooperating journal. The two motors 43a and 43b are operatively coupled together by a timing chain 45 that maintains the motors in synchronism so that the two lead screws 66a and 66b are synchronously rotated by the two motors. Activation of the motors 43a and 43b rotates the lead screws 66a and 66b in a direction determined by the controlling cylindrical coordinate data, which causes the engaged lead screw nut assemblies 67a and 67b to move in the corresponding direction along the rotated lead screws.

Each lead screw nut assembly 67a and 67b is fastened to one of the support plates 68a and 68b, the two plates serving to support the motor driven horizontal lead screw 64, cooperating lead screw nut 65 and cutting tool 53 assemblies relative to the lead screw nut assemblies 67a and 67b and cooperating lead screws 66a and 66b. The driven end of the horizontal lead screw 64 is coupled for rotation by a motor 46 fastened to the support plate 68a. The horizontal lead screw 64 extends from its driven end to an opposite end supported for rotation within a journal 47 fastened to the support plate 68b. The lead screw nut assembly 65 bears a mounting plate 69 on its upper side, upon which is fastened a motor 70 for rotating a spindle 71 that carries the cutting tool 53 for cutting the workpiece 57. Activation of the motor 46 turns the lead screw 64 in a direction determined by the controlling cylindrical coordinate data, which causes the engaging lead screw nut assembly 65 to move in the corresponding direction along the lead screw.

In the preferred embodiment of the machine tool apparatus 52, the workpiece 57 is located at one side of the structure that supports the cutting tool 53. To permit ready access to the workpiece 57 by the cutting tool 53 along radially and axially adjustable paths, the vertical lead screws 66a and 66b are horizontally displaced to one side of the horizontal lead screw 64.

Additional support for the cutting tool support and positioning apparatus is provided by four vertically extending stationary posts 72 and cooperating sleeve bearings 73. A post 72 is located at each end of each of the support plates 68a and 68b. The sleeve bearings 73 couple the support plates 68a and 68b to the posts 72 for support while permitting the support plates to move relative to the posts when the lead screws 66a and 66b are turned to move the cutting tool 53 in the axial direction, z.

The preferred machine tool apparatus 52 is arranged for constructing models of a wide variety of sizes. For this reason, the cutting tool 53 is supported by a long spindle 71 for movement over a large distance in the radial direction, r. To aid in maintaining the cutting tool 53 in the axial position specified by the cylindrical coordinate data, the spindle 71 is supported for rotational and radial movements by a journal 74 at the support plate 68b nearest the turntable 58. The journal 74 is supported by a platform 75 joined at the top edge of the support plate 68b to extend horizontally therefrom in the direction opposite the turntable 58.

The various motors of the machine-controlled contour sculpting tool apparatus 52 are synchronously controlled by the machine tool controller 63 in accordance with the cylindrical coordinate data derived from the series of oblique cross sectional representations of the mandible 10 so that the workpiece 57 is cut to have a contour corresponding to that represented by the cylindrical coordinates. More specifically, the derived cylindrical coordinate data is stored in a memory 56 for use by the machine tool controller 63 in controlling the trajectory of the cutting tool relative to the workpiece 57. The machine tool controller provides commands to a motor drive circuit 76 coupled to drive the rotary cutting tool 53 at a selected speed suitable for sculpting the workpiece 57 into the desired form and finish. In addition, the controller 63 provides commands to the three motor drive circuits 77, 78 and 79, which are coupled respectively to synchronously drive the radial position determining horizontal lead screw motor 46b, the axial position determining vertical lead screw motors 43a and 43b, and the turntable motor 59. These later commands are provided in accordance with cylindrical coordinate data so that the turntable 58 is rotated and the cutting tool 53 moved relative to the axis 62 whereby the tool follows a trajectory relative to the workpiece 57 productive of the formation of a model that accurately represents the mandible segment 51.

The machine tool controller 63 is arranged to issue commands to the axial motor drive circuit 78 to step the cutting tool 53 in increments along the rotational axis 62 of the turntable 58 so that the workpiece 57 is cut along concentric bands, with each band at a location along the axis 62 corresponding to the location of a plane along line 54 at which a cross sectional representation of the mandible 10 is obtained. In addition, the machine tool controller 63 is able to process the cylindrical coordinate data to calculate, by linear interpolation, the change in the axial coordinate z as a function of the angular coordinate θ between adjacent locations of cross sectional representations of the mandible 10. This calculation provides axial and angular coordinate data permitting the cutting tool 53 to be directed along a spiral trajectory in sculpting the workpiece 57.

The preferred embodiment of the controlled contour machine tool apparatus 52 employs stepping motors for driving the lead screws 64 and 66 and turntable 58. The apparatus 52 is controllable to rotate the turntable 58 in steps as small as fractions of an angular minute and to move the rotary cutting tool 53 in the radial, r, and axial, z, directions in steps as small as fractions of a millimeter. For constructing a prosthesis of an internal anatomic tissue structure, such as mandible 10, however, turntable rotation steps on the order of one or two degrees and cutting tool radial and axial movement steps on the order of tenths of a millimeter are satisfactory.

The preferred method of the present invention has been described in detail with reference to sculpting a corporeal model replica of a segment 51 of a mandible 10 using a machine-controlled contour sculpting tool apparatus 52 having a single cutting tool 53 controlled in accordance with cylindrical coordinates that define a three dimensional representation of the segment. However, it will be appreciated that machine-controlled contour sculpting tool apparatus arranged to control the trajectory of a cutting tool specified by three dimensional Cartesian coordinates can be employed in the method of the present invention to form the corporeal model. Moreover, machine-controlled contour sculpting tool apparatus having a plurality of independently controllable cutting tools can be used to form the corporeal model in accordance with the method of the present invention. The particular nature of the machine-controlled contour sculpting tool apparatus 52 employed to construct a corporeal model representation of a selected structure 10 internal to a body 11 does effect the generation of the three dimensional coordinate data from the cross section representations of the selected structure provided by the tomographic imaging device 13. In some applications, it may be necessary or convenient during the generation and/or use of the three dimensional coordinate data to translate the coordinate data between different coordinate systems or between different spatially oriented sets of axes in the identical coordinate system. For example, translations between the Cartesian and cylindrical coordinate systems is achieved by manipulating the coordinate data defining each cross section representation of the selected structure 10 according to the coordinate translating equations relating rectangular and polar coordinates. Translations between different spatially oriented sets of axes is achieved by manipulating the coordinate data according to vector normalization equations relating the differently orientated sets of axes.

Thus far, the method of the present invention has been described in detail as practiced to construct a corporeal model replica of the selected segment 51 of the mandible 10. It should be appreciated, however, that other model representations of a selected structure internal to a body can be constructed through the practice of the method of the present invention. For example, a mold cavity representation of the selected mandible segment 51 can be constructed from a workpiece from which one or more corporeal model replicas of the segment can be cast. To facilitate the construction of the cavity, it is made in two mating half sections extending in the direction of the line 54. The three dimensional coordinate data is generated from the cross section representations (or translated from previously generated coordinate data defining the surface 12 of the segment 51) to define a mating cavity form of each half of the surface 12. This coordinate data is employed by the machine-controlled contour sculpting tool apparatus 52 to direct the cutting tool 53 along a trajectory that produces one of the mold cavity half sections from a first workpiece 57 and the other of the mold cavity half sections from a second workpiece. In sculpting each mold cavity half section, the turntable 58 is incremented slowly to rotate the workpiece 57 about the axis 62 at a speed that permits the cutting tool 53 to cut the workpiece to the desired shape along a series of parallel radial/axial trajectories relative to the axis 62.

Another salient feature of the method of the present invention relates to the construction of altered corporeal model representations of structures internal to a body. The formation of altered model representations of internal body structures is particularly useful in the construction of surgically implantable prostheses. Often, a prosthesis is made to replace a missing anatomic structure, in which case a representation of the desired prosthesis form will not appear, for example, in the set of cross section images provided by a tomographic imaging device. In accordance with the method of the present invention, however, altered three dimensional coordinate data that defines a representation of the missing structure is generated from the act of cross section images that is obtained for use in forming a prosthetic model of the missing structure. As will become more apparent from the following detailed description, formation of altered three dimensional representations of structures is particularly useful in constructing prosthetic onlays and inlays. Coordinate transformation is one technique suited to the generation of three dimensional coordinate data for the construction of prosthetic onlays and inlays in accordance with the method of the present invention. An example of the use of coordinate transformation in the construction of a prosthetic onlay will now be described with reference to FIGS. 9A and 9B. The coordinate transformation is described as undertaken in the Cartesian coordinate system. However, such transformations can be undertaken in the cylindrical coordinate system as well.

To obtain the necessary coordinate data to construct a prosthesis of, for example, an atrophic mandible 91 illustrated in FIGS. 9A and 9B, data grids 92, 93 and 94 encompassing the atrophic segment of the mandible 91 (indicated by shading in FIG. 9A) are identified. Within the identified data grids, three dimensional X, Y, Z coordinates are established for determining the amount and nature of the desired coordinate translation. This can conveniently be accomplished with the aid of an image processor, such as the image processor marketed by Grinnell, Inc., under the model designation System 271. The Grinnell system is designed to function with a Digital Equipment Corporation (DEC) LSI-11/23 computer apparatus having industry standard I/O data communication terminals, a video terminal and monitor, graphic tablet and graphic printer. The Grinnell image processor and DEC computer apparatus form an image processing system arranged to interact with an operator for purposes of image generation and alteration. Image data can be input to the image processing system either from the graphic tablet or from external graphic data sources connected to an I/O data communication terminal of the system. For the purpose of translating the surface of the atrophic mandible 91, the cross section image representations generated by the CT/T 8800 system 8800 are converted to a data format compatible with the image processing system and input to that system for display and image manipulation purposes through an I/O data communication terminal. The image processing system is operable to display two dimensional or three dimensional perspective representations of objects. The desired coordinate translation is determined by displaying either a three dimensional representation of the atrophic mandible 91 or a sequence of two dimensional cross section representations of the atrophic mandible 91. Cross sections of the mandible generally perpendicular to its centric are preferred for this purpose. By use of the graphic tablet of the image processing system, the atrophic superior surface S of the mandible 91 extending from point 92 to point 93 is translated in the direction indicated by the arrows in FIGS. 9A and 9B to the desired new location S' to form an image of the desired altered mandible.

The translation of the atrophic superior surface S can be accomplished in one step, for example, using a three dimensional display of the atrophic mandible 91 (such as seen in FIG. 9A), or it can be done cross section-bycross section using two dimensional images of the atrophic mandible (such as seen in FIG. 9B) at locations along its centric line. In either case, the superior surface is translated by manipulating the graphic tablet instrument while observing the results of the manipulations on the video monitor and operating the image processing system to delete the atrophic surface S, represented in FIGS. 9A and 9B as a solid line bounding mandible 91, and create the translated surface S' at the location of the dotted line in FIGS. 9A and 9B.

As seen in FIGS. 9A and 9B, all coordinate points on the new surface S' are displaced relative to the corresponding locations on the atrophic surface S by a uniform distance q in the direction of the Z axis. For some prostheses, it may be necessary to move different coordinate points along the atrophic superior surface S by different amounts or by an amount that varies in the direction of a selected dimension of the structure according to a defined gradient. If the atrophic superior surface S is irregular, for example, different coordinate translation distances would be required to create a translated regular surface S'. The three dimensional coordinate representation of the desired altered mandible can be derived from the altered mandible image data present in the Grinnell image processing system in ways like those described hereinbefore with reference to the CT/T 8800 system.

Using an image processing system to translate and generate three dimensional coordinate data defining a desired altered structure has the advantage of enabling inspection and adjustment of the translation to produce the desired altered structure before generating the defining three dimensional coordinate data. When constructing implantable prostheses, for example, it is desirable to preview the translation and adjust it until the displayed altered structure mates with the displayed unaltered structure. This is helpful in constructing an implantable prosthesis that properly mates with the surrounding anatomic structures. However, the desired translation and generation can be accomplished in other ways as well. For example, new coordinate data can be obtained by manipulation of the atrophic mandible coordinate data derived from the CT/T 8800 image representations of the atrophic mandible 91. In either case, the three dimensional coordinate data specifying the altered mandible is obtained by adding a coordinate value corresponding to the distance q to the Z axis coordinate value for all specified coordinate points of the atrophic surface S.

For purposes of constructing an implantable prosthetic onlay, only the altered segment of the altered mandible 91 is required. A three dimensional coordinate specification of only the altered segment is obtained by subtracting each Z axis coordinate value defining the atrophic superior surface S from the axis coordinate value of the translated new surface S' at the corresponding X and Y coordinate locations. An implantable prosthetic onlay is formed according to the remainder coordinate values.

Models of deformed or missing segments of internal structures also can be constructed from coordinate data specifying the deformed or missing segment that is derived from representations of a normal mirror image segment of the structure. For example, coordinate data defining a mirror image segment of a structure is useful in the construction of an implantable prosthetic inlay that is to replace a missing segment of a generally symmetrical internal anatomic structure. Derivation of the mirror image coordinate data can be accomplished through the use of the above-described Grinnell image processor or by manipulation of the coordinate data derived from the data representations provided by the CT/T 8800 system 13. If the image processor is employed, the deformed, but otherwise generally symmetrical structure is displayed and the deformed or missing segment is altered to the desired form by operator manipulation of the graphic tablet, using the video monitor display of the mirror image segment of the structure as a guide. The desired three dimensional coordinate data is generated from the altered segment as described hereinbefore with reference to FIGS. 9A and 9B.

However, the mirror image coordinate data can be obtained directly from the three dimensional coordinate data defining a normal segment of an internal structure that is generated directly from the image representations provided by the CT/T 8800 system 13. Referring to FIG. 10, a deformed mandible 97 is illustrated in relation to three dimensional X, Y, Z coordinates. But for the deformation, the mandible is generally symmetrical about the Y-Z plane extending through the most anterior point 99 of the mandible 97. As seen in FIG. 10, the deformation is in the form of a missing segment 100 located at the left side of the XY plane of symmetry. A normal segment 96 of the mandible 97 exists to right of the nominal XY plane of general symmetry at the mirror image location relative to the missing segment 100. This segment 96 is surrounded by an enclosure 98 that defines data grids including the three dimensional X, Y, Z spatial coordinates defining the normal segment 96. The actual and mirror image coordinates of the normal segment 96 are the same relative to the Y and Z coordinate axes, but are different relative to the X coordinate axis. To obtain the mirror image X coordinate, the distance separating the actual X coordinate value of each coordinate point specifying the normal segment 96 from the X coordinate value of the location of the XY plane of symmetry is multiplied by $(-1)$ and is added to the X coordinate value of the location of the XY plane of symmetry. This coordinate translation technique enables the generation of the mirror image coordinate values of the normal segment 96 by manipulation of the three dimensional coordinate data generated directly from the image representations obtained by the CT/T 8800 system 13.

For convenience, the derivation of translated coordinate data has been described with reference to coordinate manipulation in the Cartesian coordinate system and cross section representations of the internal structure that are defined three dimensionally in relation to orthogonal X, Y, Z axes that are oblique to the axial, coronal and sagital planes. Translation of the coordinates from that axis orientation to any other desired axis orientation or to a cylindrical coordinate system can be accomplished as described in detail hereinbefore. However generated, three dimensional coordinate data in the form required by the machine-controlled contour sculpting tool apparatus 52 is generated from the translated representation and input to the sculpting tool apparatus to control the trajectory of the cutting tool 53 so that the desired altered corporeal model representation of the selected internal structure is formed.

The method of the present invention has been described in detail with reference to the construction of various corporeal model representations of structures internal to bodies from coordinate data obtained from reconstructed representations of contiguous cross sections of the structures. However, corporeal models can be constructed from coordinate data obtained from reconstructed representations of cross sections at spaced intervals along the structure as well. For example, a generally uniform structure, such as the femur bone, can be represented by reconstructed representations taken from widely spaced locations along its length. In such applications, the three dimensional coordinates required for the control of the sculpting tool between the widely spaced locations is generated by interpo-lation of the locations of the selected structure intermediate to the spaced locations and generating corresponding three dimensional coordinates that define the interpolated locations. The corporeal model is formed by directing the sculpting tool in accordance with the three dimensional coordinates that define the spaced and intermediate locations of the selected structures.

One preferred embodiment and certain variations of the method of the present invention have been described in detail as arranged to construct corporeal models of selected internal anatomic structures useful in the study of internal structures of anatomies and in the surgical correction of deformed internal structures. It will be apparent to those skilled in the art, however, that various modifications and changes may be made in the practice and use of the method without departing from the scope of the present invention as set forth in the following appended claims.

What is claimed is:

1. A method of fabricating a three dimensional corporeal model of a structure internal to a body, comprising:
    subjecting the body to radiant energy to produce radiant energy responses internal to said body, the radiant energy selected to produce radiant energy responses that are characteristic of a selected physical property of substances detectable exterior of the body;
    detecting produced radiant energy responses to obtain representations of substances at locations internal to the body defining structures internal to said body three-dimensionally;
    generating from the representations of the substances a set of three dimensional coordinates defining a three dimensional representation of a selected structure internal to the body; and
    directing a sculpting tool into a workpiece in accordance with the generated set of three dimensional coordinates to form a corporeal model corresponding to the three dimensional representation of the selected structure.

2. The method of claim 1 wherein the subjecting step and detecting step are performed exterior to the body in which said selected structue is located.

3. The method of claim 1, further comprising:
    displaying a visual representation of the selected structure defined by the set of three dimensional coordinates; and
    selectively adjusting the three dimensional coordinates; and wherein
    the sculpting tool is directed into the workpiece in accordance with the adjusted three dimensional coordinates.

4. The method of claim 1 wherein:
    the generated set of three dimensional coordinates defines an altered three dimensional representation of the selected structure; and
    the formed corporeal model corresponds to the altered three dimensional representation of the selected structure.

5. The method of claim 4 wherein a set of transformed three dimensional coordinates are generated from the obtained representations of the substances to define the altered three dimensional representation of the selected structure, further comprising:
    displaying a visual representation of the altered three dimensional representations of the selected structure defined by the set of transformed three dimensional coordinates; and
    selectively adjusting the transformed three dimensional coordinates; and wherein
    the sculpting tool is directed into the workpiece in accordance with the transformed and selectively adjusted three dimensional coordinates.

6. The method of either claim 3, 4 or 5 wherein:
    the generated set of three dimensional coordinates defines an ununiformly altered three dimensional representation of the selected structure; and
    the directed sculpting tool forms a corporeal model corresponding to the ununiformly altered three dimensional representation of the selected structure.

7. The method of claim 6 wherein the generated set of three dimensional coordinates defines an altered three dimensional representation of the selected structure having a selected surface segment altered in a coordinate direction to effect a unidirectional translation of a corresponding selected surface segment in the formed corporeal model.

8. The method of either claim 3, 4 or 5 wherein:
    the generated set of three dimensional coordinates defines a mirror image three dimensional representation of the selected structure; and
    the directed sculpting tool forms a corporeal model corresponding to the mirror image three dimensional representation of the selected structure.

9. The method of claim 8 wherein:
    the selected structure is a segment of a larger structure internal to the body having a nominal plane of general symmetry; and
    the generated set of three dimensional coordinates defines a three dimensional representation of a mirror image of the selected structure taken relative to a mirror plane located at the nominal plane of general symmetry.

10. The method of claim 1 wherein the selected structure is a segment of a larger structure internal to the body having a nominal plane of general symmetry, and said segment is located at one side of said nominal plane of symmetry, further comprising:
    transforming the three dimensinal coordinates generated from the obtained representations of substances to define a mirror image three dimensional representation of the segment; and wherein
    the sculpting tool is directed into the workpiece in accordance with the transformed three dimensional coordinates to form a mirror image corporeal model of the segment corresponding to the mirror image three dimensional representation.

11. The method of claim 10, further comprising:
    displaying a visual representation of the mirror image three dimensional representations of the segment defined by the transformed three dimensional coordinates; and selectively adjusting the transformed three dimensional coordinates; and wherein:

the sculpting tool is directed into the workpiece in accordance with the transformed and selectively adjusted three dimensional coordinates.

12. The method of claim 1 wherein:

the generated set of three dimensional coordinates defines a three dimensional mold cavity representation of the selected structure; and further comprising directing the sculpting tool into the workpiece to form a mold cavity in accordance with the three dimensional mold cavity representation;

casting a corporeal model replica of the selected structure defined by the mold cavity.

13. The method of claim 1 wherein:

representations of the substance are obtained for spaced locations defining surfaces of structures; and the generated set of three dimensional coordinates includes coordinates of spaced locations defining a three dimensional representation of the surface of the selected structure; and further comprising interpolating locations of the surface of the selected structure intermediate to the spaced locations and generating from said interpolations of the intermediate locations three dimensional coordinates defining the surface of the selected structure at locations between spaced locations; and wherein the sculpting tool is directed into the workpiece in accordance with the three dimensional coordinates of the spaced locations and of the interpolated locations.

14. A method of fabricating a three dimensional corporeal model of a selected structure internal to a body by a sculpting tool from three dimensional coordinates defining a three dimensional representation of said selected structure, said data obtained by subjecting the selected structure within the body to radiant energy selected to be productive of selected radiant energy responses that are characteristic of substances and detectable at the exterior of said body, detecting the radiant energy responses to obtain representations of the selected structure, and generating from the representations the three dimensional coordinates, comprising:

directing the sculpting tool into a workpiece in accordance with the generated three dimensional coordinates to form a corporeal model corresponding to the three dimensional representation of the selected structure.

15. The method of claim 14 wherein:

the generated three dimensional coordinates data define a three dimensional mold cavity representation of the selected structure; and further comprising directing the sculpting tool into the workpiece to form a mold cavity in accordance with the three dimensional mold cavity representation;

casting a material replica of the selected structure defined by the mold cavity.

16. The method of claim 14 wherein:

representations of the substances are obtained for spaced locations defining surfaces of structures;

the generated three dimensional coordinates include coordinates of spaced locations defining a three dimensional representation of the surface of the selected structure; and further comprising interpolating locations of the surface of the selected structure intermediate to the spaced locations and generating from said interpolations of the intermediate locations three dimensional coordinates defining the surface of the selected structure at locations between spaced locations; and wherein the sculpting tool is directed into the workpiece in accordance with the three dimensional coordinates of the spaced locations and of the interpolated locations.

17. A method of generating three dimensional coordinates for directing a sculpting tool to form a three dimensional corporeal model of a structure internal to a body, comprising:

subjecting the body to radiant energy to produce radiant energy responses internal to said body that are characteristic of substances and detectable at the exterior the body;

detecting produced radiant energy responses to obtain representations of substances at locations internal to the body defining structures internal to the body three dimensionally; and generating from the representations of the substances three dimensional coordinates defining a three dimensional representation of a selected structure internal of the body, the three dimensional coordinates generated for directing the sculpting tool into a workpiece to form a corporeal model corresponding to the three dimensional representation of the selected structure.

18. The method of claim 17 wherein the generated three dimensional coordinates define an altered three dimensional representation of the selected structure.

19. The method of claim 17, further comprising:

displaying a visual representation of the selected structure defined by the generated three dimensional coordinates; and selectively adjusting the three dimensional coordinates; and wherein the three dimensional coordinates generated for directing the sculpting tool correspond to the adjusted three dimensional coordinates.

20. The method of claim 19 wherein transformed three dimensional coordinates are generated from the obtained representation of the substances to define an altered three dimensional representation of the selected structure;

a visual representation of altered three dimensional representation of the selected structure is displayed; and the transformed three dimensional coordinates are selectively adjusted.

21. The method of claim 17 wherein the generated three dimensional coordinates define a three dimensional mold cavity representation of the selected structure.

22. The method of claim 17 wherein:

representations of the substances are obtained for spaced locations defining surfaces of structures; and the generated three dimensional coordinates include coordinates of spaced locations defining a three dimensional representation of the surface of the selected structure; and further comprising interpolating locations of the surface of the selected structure intermediate to the spaced locations and generating from said interpolations of the intermediate locations three dimensional coordinates defining the surface of the selected structure at locations between spaced locations; and wherein the three dimensional coordinates generated for directing the sculpting tool include the three dimensional coordinates generated from the interpolations of the intermediate locations.

23. A method of fabricating a three dimensional corporeal model of selected tissue structure internal to an anatomy, comprising:

subjecting the anatomy to radiant energy to produce radiant energy responses internal to said anatomy that are characteristic of tissue structure of said anatomy and that are detectable at the exterior of said anatomy at a plurality of locations each of which is along a path extending in a different selected direction relative to the selected tissue structure;

detecting produced radiant energy responses at the exterior of the anatomy at selected locations of the plurality of locations to obtain representations of the selected tissue structure that are definitive of a selected three dimensional representation thereof;

generating from the obtained representations of the selected tissue structure selected three dimensional coordinates defining the selected three dimensional representation of the selected tissue structure; and directing a sculpting tool into a workpiece in accordance with the generated selected three dimensional coordinates to form a corporeal model corresponding to the selected three dimensional representation of the selected tissue structure.

24. The method of claim 23 wherein transformed three dimensional coordinates are generated from the obtained representations of the selected tissue structure to define an altered selected three dimensional representation of the selected tissue structure.

25. The method of either claim 23 or claim 24, further comprising:

displaying a visual representation of the selected tissue structure defined by the three dimensional coordinates generated from the obtained representations;

selectively adjusting the generated three dimensional coordinates to define the selected three dimensional representation of the selected tissue structure; and wherein the sculpting tool is directed into the workpiece in accordance with the adjusted three dimensional coordinates.

26. The method of claim 23 as arranged to fabricate a surgically implantable prosthesis type corporeal model of a selected skeletal tissue structure of a mammalian anatomy wherein:

the mammalian anatomy is subjected to radiant energy to produce radiant energy responses at locations definitive of the surgically implantable prosthesis to be fabricated; and the generated three dimensional coordinates define a three dimensional representation of the surgically implantable prosthesis.

27. The method of claim 26 wherein the sculpting tool is directed into the workpiece to form the surgically implantable prosthesis.

28. The method of claim 26 wherein:

the generated three dimensional coordinates define a three dimensional mold cavity representation of the surgically implantable prosthesis; and the sculpting tool is directed into the workpiece to form a mold cavity in accordance with the three dimensional mold cavity representation; and further comprising casting a surgically implantable prosthesis defined by the mold cavity.

29. A method of fabricating a prosthesis representative of a selected tissue structure internal to a mammalian anatomy, comprising:

subjecting the anatomy to radiant energy; detecting exterior of said anatomy, resulting radiant energy responses produced at a plurality of parallel planes distributed at spaced locations in a selected direction relative to the said anatomy, the radiant energy selected to produce radiant energy responses internal to said anatomy that are characteristic of tissue structure of the anatomy and that are detectable from the exterior of said anatomy, the anatomy subjected to the radiant energy and resulting radiant energy responses detected to be productive of selected representations of the structure internal to the anatomy definitive of the prosthesis to be fabricated;

generating from the selected representations of the structure internal to the anatomy selected three dimensional coordinates defining a selected representation of the prosthesis; and directing a sculpting tool into the workpiece in accordance with the generated selected three dimensional coordinates to form the selected representation of the prosthesis.

30. The method of claim 29 wherein the selected representation of the prosthesis is a replica of the selected tissue structure.

31. The method of claim 29 wherein:

the generated three dimensional coordinates define a three dimensional mold cavity representation of the prosthesis; and the sculpting tool is directed into the workpiece to form a mold cavity in accordance with the three dimensional mold cavity representation; and further comprising casting a prosthesis defined by the mold cavity.

* * * * *

REEXAMINATION CERTIFICATE (862nd)
United States Patent [19]
White

[11] B1 4,436,684
[45] Certificate Issued May 31, 1988

[54] METHOD OF FORMING IMPLANTABLE PROSTHESES FOR RECONSTRUCTIVE SURGERY

[75] Inventor: David N. White, Palo Alto, Calif.

[73] Assignee: Contour Med Partners, Ltd., Mountain View, Calif.

Reexamination Request:
No. 90/001,283, Jul. 13, 1987

Reexamination Certificate for:
Patent No.: 4,436,684
Issued: Mar. 13, 1984
Appl. No.: 384,646
Filed: Jun. 3, 1982

[51] Int. Cl.⁴ .................. B23Q 33/00; A61B 6/03; A61F 2/28; B23Q 15/14
[52] U.S. Cl. .................. 264/138; 128/92 R; 128/653; 264/16; 264/163; 264/219; 364/414; 364/474; 378/4; 378/18; 378/21; 378/207; 434/82; 434/267; 434/274; 623/10; 623/11; 623/16
[58] Field of Search ........ 434/82, 267, 270, 274; 378/4–21; 128/303 B, 653, 92 R; 264/138, 163, 219, 222, 16, 17; 623/11, 16; 364/414, 474, 475

[56] References Cited

U.S. PATENT DOCUMENTS

| | | | |
|---|---|---|---|
| 3,534,396 | 10/1970 | Hart et al. | 364/474 |
| 3,932,923 | 1/1976 | DiMatteo | 364/474 |
| 4,135,247 | 1/1979 | Gordon et al. | 364/414 |
| 4,379,329 | 4/1983 | LeMay | 364/414 |

OTHER PUBLICATIONS

Lerch et al, "Development of Optical Process for Accessing Three-Dimensional Patient Topology", *Medical Physics*, vol. 5, No. 6, (Nov./Dec. 1978), pp. 546–549.

Tonner, H. et al, "A New Method for the Preparation of Special Alloplastic Implants for Partial Replacement of the Pelvis", *Fortschritte der Medizin*, (Apr. 1979), pp. 781–783.

Reinstein, L. et al, "A Computer-Assisted Three-Dimensional Treatment Planning System", *Radiation Physics*, vol. 27, (Apr. 1978), pp. 259–264.

Gerngross, H. et al, "Possibilities of Geometric X-ray Examination of Pelvis for Replacing Half of the Pelvis by an Artificial Pelvis", *Zeitschrift für Orthopädie* 118, (1980), pp. 331–336.

Alberti, C., "Three-Dimensional CT and Structure Models", *British Journal of Radiology*, v. 53 (1980), pp. 261–262.

Tatcher, M. et al, "An Analog Patient Model Derived from Computed Tomograms for Three-Dimensional Radiotherapy Planning", *Technical Notes*, (Jul. 1980), pp. 236–238.

Burri, C. et al, "Total 'Internal' Hemipelvectomy", *Archives of Orthopaedic and Traumatic Surgery*, (1979), pp. 219–226.

*Primary Examiner*—Jay H. Woo

[57] ABSTRACT

Non-invasive method of forming prostheses of skeletal structures internal to a body for use in reconstructive surgery. The selected internal skeletal structure is measured by subjecting the body to radiant energy to produce radiant energy responses that are detected to obtain representations delineating the skeletal structure. Three dimensional coordinate data defining the skeletal structure is generated from the obtained representations. The coordinate data is employed to control a sculpting tool to form the prosthesis.

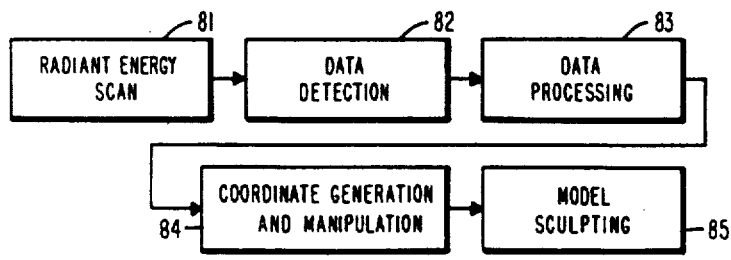

B1 4,436,684

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 14–16, 18, 20, 24 and 26–28 are cancelled.

Claims 1–10, 12, 13, 17, 19, 23, 25, 29 and 31 are determined to be patentable as amended.

Claims 11, 21, 22 and 30 dependent on an amended claim, are determined to be patentable.

New claims 32–34 are added and determined to be patentable.

1. A method of fabricating a three dimensional corporeal model of a structure internal to a body, comprising:
   subjecting the body to radiant energy to produce radiant energy responses internal to said body, the radiant energy selected to produce radiant energy responses that are characteristic of a selected physical property of substances detectable exterior of the body;
   detecting produced radiant energy responses to obtain [representations] *a plurality of two dimensional digital representations, the two dimensional digital representations being spaced along a third dimension to produce a digital data set representative* of [substances at locations internal to the body defining] *structures internal to said body three-dimensionally*;
   [generating from the representations of the substances a set of three dimensional coordinates] *selecting a particular structure internal to the body, the selecting step including selecting from among the digital data set representative of structures internal to the body a selected subject of digital coordinates defining the surface of the selected structure, the selected subset comprising three dimensional digital coordinates defining a three dimensional representation of* [a] *the* selected structure internal to the body; and
   directing a sculpting tool into a workpiece *directly* in accordance with the [generated set of] three dimensional *digital* coordinates to form a *three dimensional* corporeal model corresponding to the three dimensional representation of the selected structure.

2. The method of claim 1 wherein the subjecting step and detecting step are performed exterior to the body in which said selected [structue] *structure* is located.

3. The method of claim 1, further comprising:
   displaying a visual representation of the selected structure defined by the set of three dimensional *digital* coordinates; and
   selectively adjusting the three dimensional *digital* coordinates; and wherein
   the sculpting tool is directed into the workpiece in accordance with the adjusted three dimensional *digital* coordinates.

4. The method of claim 1 wherein:
   the [generated] *selected* set of three dimensional *digital* coordinates defines an altered three dimensional representation of the selected structure; and
   the formed *three dimensional* corporeal model corresponds to the altered three dimensional representation of the selected structure.

5. The method of claim 4 wherein a set of transformed *digital* coordinates are generated from the [obtained representations of the substances] *digital data set representative of structures internal to the body* to define the altered three dimensional representation of the selected structure, further comprising:
   displaying a visual representation of the altered three dimensional [representations] *representation* of the selected structure defined by the set of transformed three dimensional coordinates; and
   selectively adjusting the transformed three dimensional coordinates; and wherein
   the sculpting tool is directed into the workpiece in accordance with the transformed and selectively adjusted three dimensional *digital* coordinates.

6. The method of either claim 3, 4 or 5 wherein:
   the [generated] *selected* set of three dimensional *digital* coordinates defines an ununiformly altered three dimensional representation of the selected structure; and
   the directed sculpting tool forms a *three dimensional* corporeal model corresponding to the ununiformly altered three dimensional representation of the selected structure.

7. The method of claim 6 wherein the generated set of three dimensional *digital* coordinates defines an altered three dimensional representation of the selected structure having a selected surface segment altered in a coordinate direction to effect a unidirectional translation of a corresponding selected surface segment in the formed corporeal model.

8. The method of either claim 3, 4 or 5 wherein:
   the [generated] *selected* set of three dimensional *digital* coordinates defines a mirror image three dimensional representation of the selected strucuture; and
   the directed sculpting tool forms a *three dimensional* corporeal model corresponding to the mirror image three dimensional representation of the selected structure.

9. The method of claim 8 wherein:
   the selected structure is a segment of a larger structure internal to the body having a nominal plane of general symmetry; and
   the [generated] *selected* set of three dimensional *digital* coordinates defines a three dimensional representation of a mirror image of the selected structure taken relative to a mirror plane located at the nominal plane of general symmetry.

10. [The] *A* method of [claim 1] *fabricating a three dimensional corporeal model of a structure internal to a body comprising:*
    *subjecting the body to radiant energy to produce radiant energy responses internal to said body, the radiant energy selected to produce radiant energy responses that are characteristic of a selected physical property of substances detectable exterior of the body;*

*detecting produced radiant energy responses to obtain representations of substances at locations internal to the body defining structures internal to said body three-dimensionally;*

*generating from the representations of the substances a set of three dimensional coordinates defining a three dimensional representation of a selected structure internal to the body; and* directing a sculpting tool into a workpiece in accordance with the generated set of three dimensional coordinates to form a corporeal model corresponding to the three dimensional representation of the selected structure;

wherein the selected structure is a segment of a larger structure internal to the body having a nominal plane of general symmetry, and said segment is located at one side of said nominal plane of symmetry, further comprising:

transforming the three dimensional coordinates generated from the obtained representations of substances to define a mirror image three dimensional representation of the segment; and wherein the sculpting tool is directed into the workpiece in accordance with the transformed three dimensional coordinates to form a mirror image corporeal model of the segment corresponding to the mirror image three dimensional representation.

12. The method of claim 1 wherein:

the [generated] *selected* set of three dimensional *digital* coordinates defines a three dimensional mold cavity representation of the selected structure; and further comprising directing the sculpting tool into the workpiece to form a mold cavity in accordance with the three dimensional mold cavity representation;

casting a *three dimensional* corporeal model replica of the selected structure defined by the mold cavity.

13. The method of claim 1 wherein:

representations of the [substance] *structure* are obtained for spaced locations defining surfaces of structures; and the [generated] *selected* set of three dimensional *digital* coordinates includes coordinates of spaced locations defining a three dimensional representation of the surface of the selected structure; and further comprising interpolating locations of the surface of the selected structure intermediate to the spaced locations and generating from said interpolations of the intermediate locations three dimensional coordinates defining the surface of the selected structure at locations between spaced locations; and wherein the sculpting tool is directed into the workpiece in accordance with the three dimensional coordinates of the spaced locations and of the interpolated locations.

17. A method of generating three dimensional coordinates for directing a sculpting tool to form a three dimensional [corporeal model of] *prosthesis having a shape designed to interface with* a structure internal to a body, comprising:

subjecting the body to radiant energy to produce radiant energy responses internal to said body that are characteristic of substances and detectable at the exterior of the body;

detecting produced radiant energy responses to obtain representations of substances at locations internal to the body defining structures internal to the body three dimensionally; and generating from the representations of the substances three dimensional coordinates defining a three dimensional representation of a selected structure internal of the body,

*selectively altering the three dimensional coordinates to define an altered set of three dimensional coordinates of a designed prosthesis which has a configuration partly representative of the selected structure and partly altered;*

*whereby the generated three dimensional coordinates define an altered three dimensional representation of the selected structure, the altered* three dimensional coordinates generated for directing the sculpting tool into a workpiece to form a [corporeal model] *prosthesis* corresponding to the *altered* three dimensional [representation of the selected structure] *coordinates.*

19. The method of claim 17, further comprising:

displaying a visual representation of the selected structure defined by the generated three dimensional coordinates; and selectively [adjusting] *altering* the three dimensional coordinates *while visually observing the displayed result of the selective alteration* [; and wherein the three dimensional coordinates generated for directing the sculpting tool correspond to the adjusted three dimensional coordinates].

23. A method of fabricating a three dimensional [corporeal model of] *prosthesis having a shape designed to interface with* selected tissue structure internal to an anatomy, comprising:

subjecting the anatomy to radiant energy to produce radiant energy responses internal to said anatomy that are characteristic of tissue structure of said anatomy and that are detectable at the exterior of said anatomy at a plurality of locations each of which is along a path extending in a different selected direction relative to the selected tissue structure;

detecting produced radiant energy responses at the exterior of the anatomy at selected locations of the plurality of locations to obtain representations of the selected tissue structure that are definitive of a selected three dimensional representation thereof;

generating from the obtained representations of the selected tissue structure selected three dimensional coordinates defining the selected three dimensional representation of the selected tissue structure; [and]

*selectively altering the three dimensional coordinates to define an altered set of three dimensional coordinates of a designed prosthesis which has a configuration partly representative of the selected tissue structure and partly altered; and* directing a sculpting tool into a workpiece in accordance with the [generated selected] *altered set of* three dimensional coordinates to form a [corporeal model corresponding to the selected three dimensional representation of] *prosthesis having a shape designed to interface with* the selected tissue structure.

25. The method of [either] claim 23 [or claim 24] further comprising:

displaying a visual representation of the selected tissue structure defined by the three dimensional coordinates generated from the obtained representations;

selectively [adjusting] *altering* the generated three dimensional coordinates [to define the selected three dimensional representation of the selected tissue structure; and wherein the sculpting tool is directed into the workpiece in accordance with the adjusted three dimensional coordinates] *while visually observing the displayed result of the selective alteration.*

29. A method of fabricating a prosthesis representative of a selected tissue structure internal to a mammalian anatomy; comprising:

subjecting the anatomy to radiant energy; detecting exterior of said anatomy, resulting radiant energy responses produced at a plurality of parallel planes distributed at spaced locations in a selected direction relative to the said anatomy, the radiant energy selected to produce radiant energy responses internal to said anatomy that are characteristic of tissue structure of the anatomy and that are detectable from the exterior of said anatomy, the anatomy subjected to the radiant energy and resulting radiant energy responses detected to be productive of selected representations of the structure internal to the anatomy definitive of the prosthesis to be fabricated;

generating from the selected representations of the structure internal to the anatomy selected three dimensional coordinates defining a selected representation of the [prosthesis] *selected structure*; [and]

*selectively altering the three dimensional coordinates to define an altered set of three dimensional coordinates of a designed prosthesis which has a configuration partly representative of the selected structure and partly altered; and* directing a sculpting tool into the workpiece in accordance with the [generated selected] *altered set of* three dimensional coordinates to form the selected representation of the prosthesis.

31. The method of claim 29 wherein:

the [generated] *altered* three dimensional coordinates define a three dimensional mold cavity representation of the prosthesis; and the sculpting tool is directed into the workpiece to form a mold cavity in accordance with the three dimensional mold cavity representation; and further comprising casting a prosthesis defined by the mold cavity.

*32. A method of fabricating a three dimensional prosthesis having a shape designed to interface with a structure internal to a body, comprising:*

*subjecting the body to radiant energy to produce radiant energy responses internal to said body, the radiant energy selected to produce radiant energy responses that are characteristic of a selected physical property of substances detectable exterior of the body;*

*detecting produced radiant energy responses to obtain representations of substances at locations internal to the body defining structures internal to said body three-dimensionally;*

*generating from the representations of the substances a set of three dimensional coordinates defining a three dimensional representation of a selected structure internal to the body;*

*selectively altering the three dimensional coordinates to define an altered set of three dimensional coordinates of a designed prosthesis which has a configuration partly representative of the selected structure and partly altered; and*

*directing a sculpting tool into a workpiece in accordance with the altered set of three dimensional coordinates to form a prosthesis having a shape designed to interface with the selected structure.*

*33. The method of claim 32 further comprising:*

*displaying a visual representation of the selected structure defined by the set of three dimensional coordinates; and*

*wherein the step of selectively altering includes interactively altering the three dimensional coordinates while visually observing the displayed result of the alteration.*

*34. The method of claim 32 wherein:*

*the radiant energy responses produced in the detecting step comprise a digital data set representative of structures internal to the body; and*

*the three dimensional coordinates produced by the generating step are selected from said digital data set.*

* * * * *